(12) United States Patent  
Roberts et al.

(10) Patent No.: US 6,841,536 B2  
(45) Date of Patent: Jan. 11, 2005

(54) PRODRUGS AND CONJUGATES OF THIOL- AND SELENOL-CONTAINING COMPOUNDS AND METHODS OF USE THEREOF

(75) Inventors: Jeannette C. Roberts, Salt Lake City, UT (US); Britta H. Wilmore, Salt Lake City, UT (US); Pamela B. Cassidy, Salt Lake City, UT (US); Pamela K. Dominick, Salt Lake City, UT (US); Megan D. Short, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 10/051,463

(22) Filed: Jan. 18, 2002

(65) Prior Publication Data

US 2003/0225255 A1 Dec. 4, 2003

Related U.S. Application Data

(63) Continuation of application No. 09/485,321, filed as application No. PCT/US98/16324 on Aug. 6, 1998, now Pat. No. 6,340,746.
(60) Provisional application No. 60/055,019, filed on Aug. 7, 1997.

(51) Int. Cl.[7] .................. A61K 31/41; A61K 31/70; C07H 15/00; C07D 305/12; C07C 205/00

(52) U.S. Cl. ............... 514/23; 514/25; 514/360; 536/17.4; 536/17.5; 536/17.6; 536/17.9; 549/315; 549/408; 549/553

(58) Field of Search .................. 536/17.4, 17.5, 536/17.6, 17.9; 549/315, 408; 562/503, 553; 514/23, 25, 360

(56) References Cited

U.S. PATENT DOCUMENTS

| | | | | |
|---|---|---|---|---|
| 4,011,221 | A | 3/1977 | Sakakibara et al. | 260/252 |
| 4,617,189 | A | 10/1986 | Stockel et al. | 424/162 |
| 4,868,114 | A | 9/1989 | Nagasawa et al. | 435/112 |
| 5,578,470 | A | 11/1996 | Kerkenaar et al. | 435/130 |
| 5,667,791 | A | 9/1997 | Hersh et al. | 424/401 |
| 6,340,746 | B1 * | 1/2002 | Roberts et al. | 536/17.4 |

FOREIGN PATENT DOCUMENTS

| | | |
|---|---|---|
| EP | 0 277 688 B1 | 10/1993 |
| WO | WO 91/02741 | 3/1991 |

OTHER PUBLICATIONS

R. L. Walters et al., "Modulation of Radiation–Induced Apoptosis by Thiolamines" Int. J. Radiat. Biol. 1997, vol. 72, No. 4, 439–448, (published Oct. 1997).

(List continued on next page.)

Primary Examiner—Elli Peselev  
(74) Attorney, Agent, or Firm—Needle & Rosenberg, PC

(57) ABSTRACT

Disclosed is a prodrug of the formula:

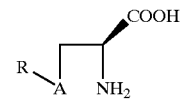

where A is a sulfur or a selenium, and R is derived from a mono- di- or oligo- saccharide.

Also disclosed is a prodrug of the formula:

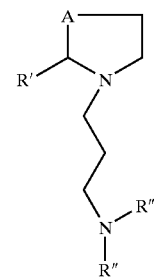

where A is sulfur or selenium, R' is derived from a sugar and R' has the formula $(CHOH)_n CH_2OH$, where n is 1 to 5, or R' is an alkyl or aryl group, or R' is =O, and the R" groups may be the same or different and may be hydrogen, alkyl, alkoxy, carboxy.

Also disclosed is a conjugate of an antioxidant vitamin and a thiolamine or selenolamine.

Also disclosed is a prodrug of the formula;

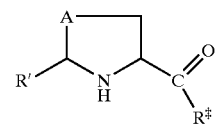

where A is sulfur or selenium, and R' is derived from a sugar and R' has the formula $(CHOH)_n CH_2OH$, where n is 1 to 5, or R' is also be an alkyl or aryl group, or R' is =O, and R[‡] is an alkoxy, or an amine group.

Also disclosed is a prodrug of the formula:

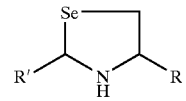

where R is COOH or H, and R' is derived from a sugar and R' has the formula $(CHOH)_n CH_2OH$, where n is 1 to 5, or R' is an alkyl or aryl group, or R' is =O.

10 Claims, No Drawings

OTHER PUBLICATIONS

J. L. Robers, et l. "Thiazolidine Prodrugs of Cysteamine and Cysteine and Radioprotective Agents" Radiation Research, 143, 203 (1995).

Carroll, M, et al. "Efficacy of Radio Protective Agents in Preventing Small and Large Bowel Radiation Injury" Dis Colon Rectum, Jul. 1995, pp. 716–722.

J. Roberts, et al. "Chemoprotection Against Cyclophosphamide–Induced Urotoxicity" Anticancer Reasearch 14: 389–396 (1994).

J. Roberts, et al. "Chemoprotection Against Cyclophosphaminde–Induced Urotoxicity: Ribose–Cysteine" Anticancer Research 14: 383 388 (1994).

Rowe, et al. "Protective Effect of Ribcys Following High–Dose Irradiation of the Rectosigmoid" vol. 56, No. 7681–687.

J. Roberts, et al. "Mechanisms of Chemoprotection by Ribcys, A Thiazolidine Prodrug of L–Cysteine" Med. Chem.Res. (1991) 213–219.

J. Roberts, et al. "Time Course for the Elevation of Gluthahione in Numerous Organs of L1210–Bearing CDFI Mice Given the L–Cysteine Prodrug, Ribcys" Toxicology Letters, 59(1991) 245–251.

J. Roberts "L–Cysteine Prodrug Protects Against Cyclophasphanimde Urotoxicity Without Compromising Therapeatuc Activity" Cancere Chemother Pharmocal (1191) 28: 166–170.

J. Roberts "Prodrugs of L–Cysteine as Protective Agetns Against Acetaminophen–Induced Hepatotoxicity" Journal of Medicinal Chemistry, 1987, vo. 30, No. 10.

Baran E. and Drabarek, S. "Studies on Synthesis of S–Glycosidic Bond Between Cysteine and Glucose or Galactose" Polish J. Chem. 52:941–946, 1978.

Draguet, C. and Renson, M. "Synthese de la Selenazolidine, de N–Alcoylselenazolidines et de Leurs Derives de Substitution en 2" Bull. Soc. Chim. Belges 81:279–287, 1972.

Hildesheim et al. "Etude de l'inhibition d'une t–ARN $N_2$–guanine methyl transferase de foie de lapin par des analogues de la S–adenosyl homocysteine" Biochimie 54:989–995, 1972.

Käsbeck, L. and Kessler, H. "Synthesis of S–α–D–Glucosylated L–Cysteine—A Novel S–Glycosyl Amino Acid" Liebigs Ann/Recueil 165–167, 1997.

Monsigny et al. "Synthèse d'un nouveau type de glycoconjuguè Le thio–β–D–glucopyranoside de la L–cystèine" Carbohydrate Res. 59:589–593, 1977.

Roberts et al. "Differential Chemoprotection Against Acetaminophen–Induced Hepatotoxicity by Latentiated L–Cysteines" Chem. Res. Toxicol. Sep. 1998.

Schneider, F. and Geyer, Hans–Ulrich "Verknüpfung von Zuckern mit Aminosäureestern lipophiler Alkohole zu grenzflächenaktiven Zuckerderivaten" Bd 330;182–187, 1963.

Tanaka et al. "WS1279, A Novel Lipopeptide Isolated from Steptomyces willmorei Biological Activities" J. Antibiotics 46(11):1699–1706, 1993.

Baruchel et al. "In vivo Selective Modulation of Tissue Glutathione in a Rat Mammary Carcinoma Model" Biochem. Pharmacol 50(9):1505–1508, 1995.

Bezlepkin et al. "The Prolongation of Survival In Mice by Dietary Antioxidants Depends on their Age by the Start of Feeding this Diet" Mechanisms of Ageing and Development 92:227–234, 1996.

Bohm et al. "A Feasibility Study of Cisplatin Administration with Low–Volume Hydration and Glutathione Protecting in the Treatment of Ovarian Carcinoma" Anticancer Res 11:1613–1616, 1991.

Cal et al. "Biochemical and Morphological Changes in the Lenses of Selenium and/or Vitamin E Deficient Rats" Biomed. And Environ. Sci. 7:109–115 , 1994.

Clark et al. "Effects of Selenium Supplementation for Cancer Prevention in Patients with Carcinoma of the Skin" JAMA 276(24):1957–1963, Dec. 25, 1996.

Crary et al. "Potential Clinical Applications for High–Dose Nutritional Antioxidants" Medical Hypotheses 13:77–98, 1984.

Dorr, Robert "Chemoprotectants for Cancer Chemotherapy" Seminars in Oncology vol. 18, No. 1, Suppl 2, pp 48–58, Feb. 1991.

El–Bayourny et al. "Chemoprevention of Cancer by Organoselenium Compounds" J. Cell. Biochem. Supplement 22:92–100, 1995.

Konstantinov et al. "Antitumor, Nephrotoxic and Clastogenic Effect of cis–DDP with DDTC or NAC" Neoplasma 41(5):253–258, 1994.

Kumar et al. "Radioprotection by Antioxidant Enzymes and Enzyme Mimetics" Pharmac. Ther. 39:309—309, 1988.

Lautermann et al. "Glutathione Protection against Gentamicin Ototoxicity Depends on Nutritional Status" Hearing Research 86:15–24, 1995.

Nagasawa et al. "Prodrugs of L–Cysteine as Liver–Protective Agents, 2(RS)–Methylthiazolidine4R–Carboxylic Acid, a Latent Cysteine" J. Med. Chem. 25(5):489–491, May 1982.

Steare, SE and Yellon, DM "The Potential for Endogenous Myocardial Antioxidants to Protect the Myocardium Against Ischaemia–Reperfusion Injury: Refreshing the Parts Exogenous Antioxidants Cannot Reach?" J. Mol. Cell. Cardiol. 27:65–74, 1995.

M. Tamba "Role of Thiols in Radioprotection: Radiation Chemical Aspects" J Biosci. 44c:857–862, 1989.

Waters et al. "Antimutagenicity Profiles for Some Model Compounds" Mutation Res. 238:57–85, 1990.

* cited by examiner

PRODRUGS AND CONJUGATES OF THIOL- AND SELENOL-CONTAINING COMPOUNDS AND METHODS OF USE THEREOF

RELATED APPLICATIONS

This application is a continuation of from U.S. patent application Ser. No. 09/485,321, now U.S. Pat. No. 6,340, 746B1, filed Jul. 20, 2002, titled "PRODRUGS AND CONJUGATES OF THIOL- AND SELENOL-CONTAINING COMPOUNDS AND METHODS OF USE THEREOF" nationalized from PCT/US98/16324 filed Aug. 6, 1998, which claimed priority to U.S. Provisional Patent Application 60/055,019, filed Aug. 7, 1997 (which applications are hereby incorporated by reference).

FIELD OF THE INVENTION

The present invention relates to sulfur- and selenium-containing compounds and methods for using these compounds to protect mammals from toxic insults. More specifically, the present invention relates to prodrugs and conjugates of thiol- or selenol-containing compounds, such as cysteine, cysteamine, glutathione, selenocysteine, selenocysteamine, and the Walter Reed (WR) compounds.

BACKGROUND OF THE INVENTION

Technical Background

Thiol- or selenol-containing compounds, e.g., cysteine, cysteamine, glutathione, selenocysteine, selenocysteamine, and the WR compounds, are known protective and preventive agents. Potential protective or preventive uses of such agents are widespread, as in reducing the unwanted side effects of chemo- or radiotherapy of cancer, improving cardiovascular function, preventing mutagenesis, preventing the initiation and/or progression of cancer, reducing toxic consequences of planned or unplanned radiation or chemical exposures, slowing the aging process, and preventing cataract formation. New evidence also links these compounds to altered gene expression and enhanced cellular repair processes.

The activity of these thiol- or selenol-containing compounds is mainly due to the sulfur or selenium atom participating in nucleophilic attack on toxic electrophiles, scavenging free radicals, effecting repair of damaged targets through hydrogen atom donation, altering the redox status of the cell, or affecting gene transcription or protein function.

For example, the reduced form of glutathione (Glu-Cys-Gly), a naturally occurring tripeptide with a free sulfhydryl group (SH), serves as a sulfhydryl buffer that maintains the cysteine residues of hemoglobin and other proteins in a reduced state. Glutathione also plays a key role in detoxifying the body by reacting with both endogenous and exogenous compounds, such as hydrogen peroxide and other peroxides.

Evidence suggests that glutathione is useful at protecting the body from the harmful side effects of radiation and chemotherapy that often accompany cancer treatment. Cyclophosphamide (CTX), for example, is a widely used antitumor agent whose clinical utility is limited by its bladder toxicity. During CTX metabolism in the body, a compound, acrolein, is released. Acrolein is thought to be responsible for the urotoxicity of CTX. Glutathione has been implicated in CTX detoxification by conjugating to acrolein.

It has been of significant interest in the art, therefore, to increase glutathione synthesis especially during periods of toxic insults. L-cysteine, a reactant in normal glutathione biosynthesis, is known to increase the synthesis of endogenous glutathione. To date, a significant challenge in the art has been to provide L-cysteine to cells at sufficiently high levels to drive glutathione biosynthesis. As disclosed, for example, in U.S. Pat. No. 4,868,114 to Nagasawa et al., prodrugs of L-cysteine (i.e., chemical compounds converted to L-cysteine in the cell), such as RibCys, can be used by the cell to drive glutathione biosynthesis shown below.

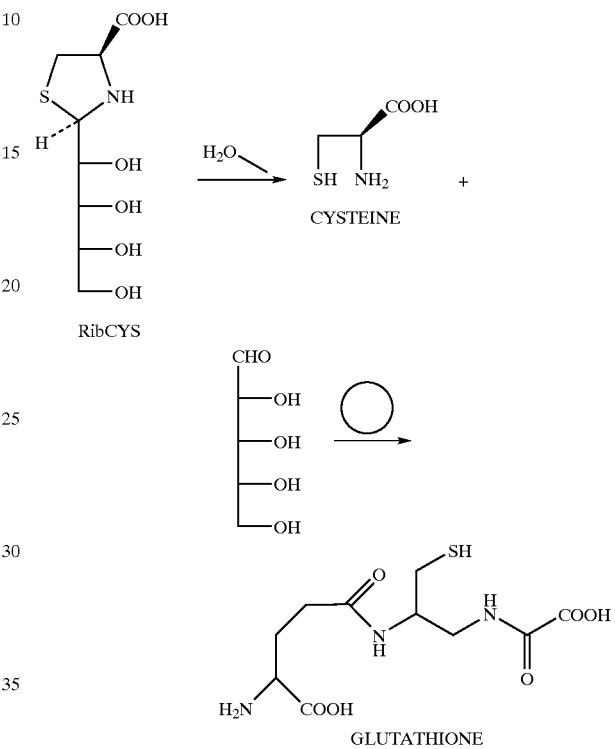

These prodrugs have been shown to offer good protection against a variety of toxic insults. However, the initial prodrugs are highly water soluble and are rapidly excreted by the body.

WR compounds are also of significant interest in the art. Over 4400 WR compounds were prepared and tested at the Walter Reed Army Hospital after World War II in an effort to develop radioprotective compounds that might be employed by military personnel during a nuclear encounter. The single agent with the greatest potential that arose from that extensive effort was WR-2721, which is converted to WR-1065 by enzymatic cleavage. These compounds have several shortcomings, however, including that they possess noteworthy toxicity and little oral activity, greatly reducing their clinical utility.

Finally, selenocysteine are of significant interest in the art for their antioxidant and anticancer properties. In fact, selenium has received significant attention for its ability to inhibit or delay the onset of AIDS caused by HIV infection. Selenium is also a cofactor of glutathione peroxidase, an enzyme which has been implicated in many detoxifying processes.

Selenium is an essential mineral that is critical to the normal functioning of many species, including humans. It also has demonstrated activity as a cancer chemopreventive agent. Selenium-containing compounds appear to have especially high preventive activity against the initiation phase of colorectal cancer, although its chemoprotective ability has been extended to cancers in many organs, caused by a variety of carcinogens.

To achieve this chemopreventive activity, levels of selenium at least five-fold greater than that required for normal nutritional status appear to be necessary. In addition, selenium must be given continuously for maximum inhibition. Unfortunately, selenium is also known for its profound toxicity, making selenium supplementation a distinct challenge.

Current selenium supplements rely on inorganic forms, such as sodium selenite ($Na_2SeO_3$) or sodium selenate ($Na_2SeO_4$). While these forms have some value, they are considered more toxic than necessary, and are unlikely to be useful in cancer chemo-prevention. Several organoselenium compounds, which appear to be less toxic in general than the inorganic forms, have been proposed for in vivo use, but the full potential of this strategy has not yet been realized. In general, however, it is very clear that the chemical form in which selenium is introduced consistently shows a marked influence on biological outcomes, including cancer chemo-prevention and toxicity.

Selenocysteine is an organic form that is present in the body and is now recognized as the 21st amino acid used in protein synthesis. While it represents a valuable biochemical form, selenocysteine is chemically unstable and difficult to handle, which has undoubtedly deterred its study and use. In addition, even though it possesses greatly reduced inherent toxicity, it still may be too toxic at chemopreventive doses to the therapeutically useful. Accordingly, prodrug forms of selenocysteine that possess reduced inherent toxicity and improved physicochemical properties would be desirable.

Objects of the Invention

It is, therefore, an object of the invention to provide prodrugs and conjugates of thiol- or selenol-containing compounds, such as cysteine, cysteamine, glutathione, selenocysteine, selenocysteamine, and the WR compounds.

Another object of the invention is to provide such thiol- or selenol-containing compounds displaying reduced toxicity and increased clinical utility.

Another object of the invention is to provide such thiol- or selenol-containing compounds with increased lipophilicity that can target a specific organ or region of the body.

Another object of the invention is to provide such thiol- or selenol-containing compounds that can be conjugated to antioxidants, such as vitamin C and E, thus maximizing the effects by providing different agents that work by complementary mechanisms.

Further objects of the invention will become evident in the description below.

BRIEF SUMMARY OF THE INVENTION

The present invention is directed to novel prodrugs and conjugates of thiol- or selenol-containing compounds, including cysteine, cysteamine, glutathione, selenocysteine, selenocysteamine, and the WR compounds. Potential protective or preventive uses of such agents are widespread, as in reducing the unwanted side effects of chemo- or radiotherapy of cancer, improving cardiovascular function, preventing mutagenesis, preventing the initiation and/or progression of cancer, reducing toxic consequences of planned or unplanned radiation or chemical exposures, slowing the aging process, preventing cataract formation, etc.

Prodrugs are inactive forms of a parent drug that have been created to overcome one or more barriers to their effective use. In the present invention, prodrugs have been designed to overcome the chemical instability and/or possible toxicity barriers that exist with the parent drug.

In one embodiment, the invention relates to the design, synthesis, and evaluation of prodrugs of L-cysteine and L-selenocysteine, containing a thioglycoside or selenoglycoside on the free thiol or selenol. The protecting group will, in addition to protecting the thiol or selenol from oxidation, permit the targeting of specific sites within the body.

For example, the galactose protected cysteine shown below will target the liver and will enter the cytoplasm of hepatocytes. Delivering L-cysteine to hepatocytes has numerous uses, including protection against hepatotoxins, such as acetaminophen, and against side effects caused by local radiation treatments.

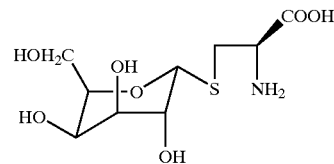

The cysteine/selenocysteine prodrugs can be depicted by the formula:

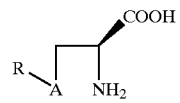

where A is a sulfur or a selenium, and R is derived from a mono- di- or oligo- saccharide, such as ribose, galactose, glucose, or mannose.

A second embodiment relates to the design, synthesis, and evaluation of novel prodrugs that are derivatives of cysteamine or selenocysteamine, such as of WR compounds, particularly WR-1065. The prodrug strategy is similar to that employed for L-cysteine, using a protecting group R'. R is typically a sugar, such as ribose. The modified WR prodrugs have numerous uses including protection against the side effects of radiation and chemotherapy, radiation and chemical induced mutations, such as from exposure to radiation during a nuclear accident or chemical spill, and even spontaneous mutations which are the cause of most cancers.

These prodrugs can be described by the formulas;

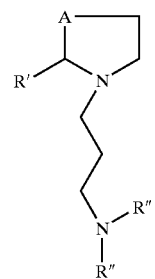

where A is sulfur or selenium, R' is derived from a sugar and has the formula $(CHOH)_nCH_2OH$, where n is 1 to 5. R' may also be hydrogen, an alkyl or aryl group, such as methyl, ethyl, benzyl, carboxyl, polyhydroxyalkyl, or phenyl, or may also be =O. The R" groups may be the same or different and may be alkyl, alkoxy, carboxy, such as acetyl, methyl or ethyl.

These novel thio- and selenol-containing compounds overcome several problems facing the art, including toxicity, water-solubility, and lack of target specificity. First, the protective or preventive activity and clinical utility will be greatly enhanced by converting the cysteine, cysteamine, glutathione, selenocysteine, selenocysteamine, and WR compounds, to thiazolidine and selenazolidone prodrug forms. These prodrugs provide a slow release form of the thiol-/selenol-amine, which greatly reduces observed toxicity (with related compounds), but provides the active agent after enzymatic or non-enzymatic biotransformation In a third embodiment, the invention relates to the design, synthesis, and evaluation of novel covalent conjugates of thiolamines or selenolamines and antioxidant vitamins, e.g., Vitamin E and Vitamin C. These compounds include conjugates of any of the prodrug compounds of the invention defined above conjugated with Vitamin C or Vitamin E. Also contemplated by the invention are conjugates of antioxidant vitamins with the following thiol- and selenol-amines and derivatives thereof; cysteine, cystine, cysteamine, cystamine, glutathione, selenocysteine, selenocysteamine, selenocystine, selenocystamine, and WR compounds (WR-1065 and WR-33278).

An example, shown below is a conjugate of cysteamine and Vitamin C.

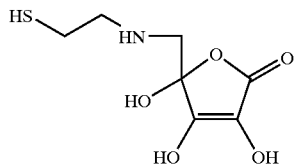

These compounds are effective because protective or preventive treatment of toxic insult will be far more effective if thiol- or selenol-containing compounds are delivered together with antioxidants such as vitamin C and E which also play a protective and preventative action in the body. The complementary mechanisms of these compounds would increase the overall effectiveness of treatment.

In yet another embodiment, the invention relates to the design, synthesis, and evaluation of novel L-cysteine prodrugs which have been modified with ester or amine groups at the carboxylic acid position. These can be described by formula;

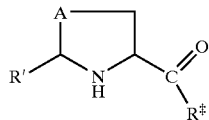

where A is sulfur or selenium, and R' is derived from a sugar and has the formula $(CHOH)_nCH_2OH$, where n is 1 to 5. R' may also be an alkyl or aryl group, such as methyl, ethyl, benzyl, carboxyl, or phenyl, or may also be =O. R$^‡$ is an alkoxy, such as $—OR^1$ where $R^1$ is ethyl, methyl. R$^‡$ may also be an amine group ($—NR^+_2$) where the R$^+$ groups are the same or different and hydrogen or an alkyl group, such as methyl.

Yet another embodiment of the invention is the condensation product of a selenolamine and a carbonyl donor characterized by the formula:

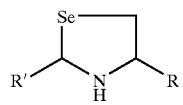

where R is COOH (prodrug of L-selenocysteine) or is H (prodrug of selenocysteamine). R' is derived from a sugar and has the structure $(CHOH)_nCH_2OH$, and where n is 1 to 5; or R' is an alkyl or aryl group, such as methyl, ethyl, benzyl, carboxyl or phenyl; or R' is =O.

DETAILED DESCRIPTION OF THE INVENTION

I. Thioglycoside Prodrugs

1. Agent Design

Prodrugs of L-cysteine and L-selenocysteine containing a thioglycoside or selenoglycoside on the free thiol or selenol can be prepared. The protecting group will, in addition to protecting the thiol or selenol from oxidation, permit the targeting of specific sites within the body.

For example, a galactose protected cysteine will target the liver and will enter the cytoplasm of hepatocytes. Delivering L-cysteine to hepatocytes has numerous uses, including protection against hepatotoxins, such as acetaminophen, and against side effects caused by local radiation treatments.

2. Chemical Synthesis.

The prodrug of L-cysteine (compound 1) was prepared as shown in Scheme 1. The protected thiogalactose analog 2 was alkylated with L-serine beta-lactone 3 in the presence of potassium carbonate. The protected thiopyranoside 4 was isolated in 70% yield after purification by silica gel chromatography. The acetate protecting groups were removed by treatment of 4 with methanolic ammonia, giving 5. Sodium in liquid ammonia was then used to remove the amino protecting groups, giving the target prodrug 1.

Scheme I

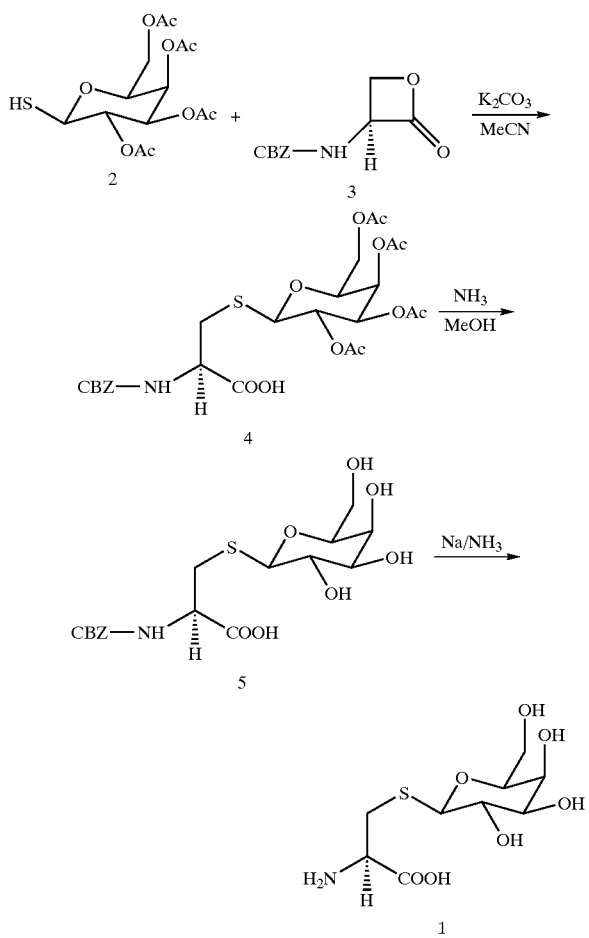

An alternative route to prodrug 1 features the formation of the thiopyranoside bond by displacement of iodine from a suitably protected galactosyl iodide (Scheme II). This route would eliminate the need to prepare beta-lactone 3 (the purification of which is difficult and not very versatile with respect to the range of I-amino protecting groups that can be used) and makes it possible to use hydroxyl (on the sugar) and amino (on the cysteine) protecting groups that can be removed in a single reaction to generate the target compound 1.

Scheme II

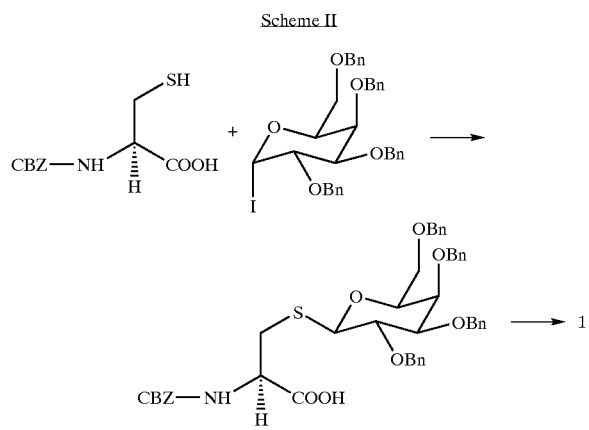

II. Thiazolidine Prodrugs of Walter Reed (WR) Compounds

1. Agent Design

Thiazolidine prodrug forms can be prepared from the thiolamine and virtually any carbonyl-containing compound, particularly the sugars, such as aldose monosaccharide, D-ribose, as an aldehyde that results in thiazolidines with superior protective activity. Numerous sugars or alkyl/aryl aldehydes or ketones can be used. These product thiazolidines will undergo non-enzymatic dissociation to liberate the active thiolamine. In addition, the 2-oxo derivatives, can be prepared, which require enzymatic action to liberate the active thiolamine.

2. Chemical Synthesis a. 2-Thiazolidinone (prodrug of cysteamine and starting material for other syntheses)

Carbonyl diimidazole (15.75 g 0.097 mol) was dissolved, with heating, in 150 ml acetonitrile, which has been degassed and flushed with nitrogen. To this was added, cysteamine hydrochloride (10.01 g, 0.088 mol), potassium carbonate (13.50 g, 0.098 mol), and 18-crown-6 (catalytic amount), and the solution was stirred at reflux (~80° C.) for 19 hours. After this time, solvent was removed in vacuo. The crude product was redissolved in 100 ml 5% sodium carbonate and refluxed for 1 hour, then acidified to pH 2 with concentrated hydrochloric acid. The resulting solid was removed via filtration and the product was extracted from the filtrate into ethyl acetate (12×35 ml). The combined organic portion was washed with 1 M potassium chloride and saturated sodium chloride (50 ml each), dried over sodium sulfate, filtered, and dried in vacuo. Yield was 84 g, 42%.

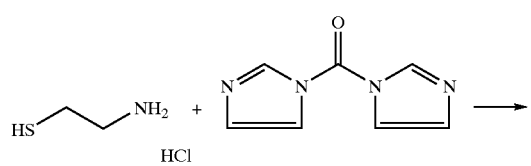

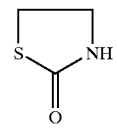

b. (N',N'-Dimethyl-3-aminopropyl)-2-thiazolidinone

To a solution of 2-thiazolidinone (4.15 g, 40.18 mmol) in acetonitrile (60 ml) were added potassium carbonate (13.3 g 96.2 mmol), N,N-dimethyl-3-aminopropyl chloride hydrochloride (7.63 g, 48.3 mmol), and 18-crown-6 (catalytic amount). The mixture was refluxed for 18 hours, solvent removed in vacuo, then redissolved in dichloromethane and 1 M potassium chloride (40 ml each). The aqueous phase was isolated and extracted twice with 30 ml portions of dichloromethane. The combined organic fraction was washed with saturated sodium chloride (~50 ml), dried over sodium sulfate, filtered, and dried in vacuo. The crude product was purified via silica gel chromatography, using a 10:1 ratio of silica gel A, 200–425 mesh, and eluting with 5% methanol in chloroform, yielding 1.15 g (15%) pure product.

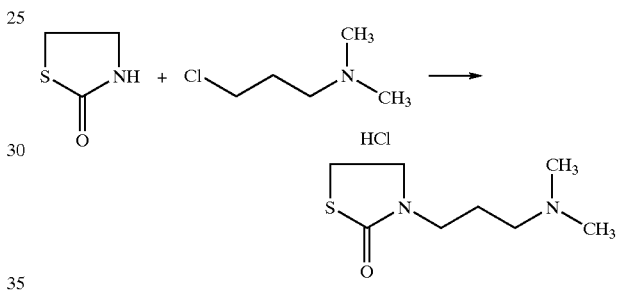

c. 3-(3-Aminopropyl)-2-thiazolidinone

To a solution of 2-thiazolidinone (0.994 g, 9.64 mmol) in acetonitrile (10 ml) were added N-phthalimido-3-bromopropylamine (2.88 g, 10.7 mmol), potassium carbonate (1.64 g, 11.9 mmol), and 18-crown-6 (catalytic amount). The mixture was refluxed about 17 hours, solvent was removed in vacuo, and the resulting solid was redissolved in 1 M potassium chloride and dichloromethane (~25 ml each). The aqueous phase was separated and extracted with 2×25 ml dichloromethane. The combined organic fraction was dried over sodium sulfate, filtered, and dried in vacuo. The crude product was recrystallized from acetone/methanol to give 1.54 g (55% yield). To a warmed solution of the phthalimido protected amine (1.53 g, 5.27 mmol) in 6:1 isopropanol:water was added sodium borohydride (1.01 g, 26.7 mmol), and the mixture was stirred at 60° C. for 22 hours. Glacial acetic acid (5.4 ml) was added, and the solution was stirred at 80° C. for 2 hours, then the solution was cooled and dried in vacuo. The product was redissolved in 6 N hydrochloric acid, washed with ether (2×30 ml), then dried in vacuo. The product was purified via recrystallization from hot water.

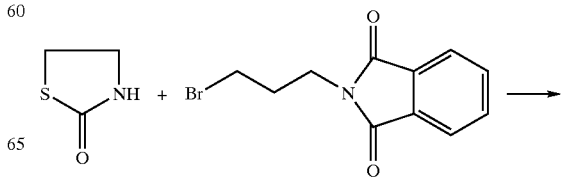

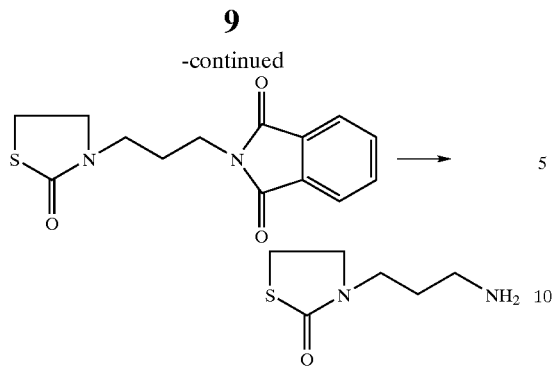

Similar procedures are employed to produce the terminal monomethylated form, as well as the terminal N-acetyl compound. In addition, various allyl or aryl aldehydes or ketones are employed to produce the corresponding allyl or aryl substituent at the 2 position, as opposed to the 2-oxo derivatives presented above.

Radioprotection in *E. coli* AB1157

A well characterized bacterial system was used as an initial screen for radioprotective activity of the novel compounds. A single colony of the bacteria, growing on a plate of LB medium (10 g tryptone, 5 g yeast extract, plus 5 g NaCl in 1 L water), was inoculated into 2 mL LB and incubated overnight. 20 mL LB medium were then inoculated with 600 μL of the overnight culture, and incubated with shaking at 37° C., 250 rpm. The cells were collected and washed with phosphate buffered saline. At this point the bacteria could be irradiated, treated with drug, etc., as outlined below. After dilution of the treated cells to 100 cells per 100 μL, they are plated out and incubated overnight. Cell viability is then measured by colony forming ability.

Growth curves were generated for the bacteria in the absence of any treatment to provide experience with basic handling as well as important baseline information. The radiation dose response of the system was investigated irradiating bacterial cultures in a Shepherd Mark I $^{137}$Cs irradiator over a dose range of 0 to 1 kGy. The dose-response curves are linear and reproducible from day to day. From these data, a radiation dose of 0.6 kGy was chosen for the initial radioprotection experiments in order to achieve approximately a 0.1% survival in the unprotected cultures, a common target for these types of studies.

The toxicity of the compounds of interest in this system was explored. Administering the 2-oxocysteamine prodrug completely eliminated the profound toxicity observed with cysteamine itself; neither WR-1065 nor its 2-oxo prodrug produced any toxicity in this assay.

Radioprotection experiments were also conducted in the bacterial system. For these experiments, the bacteria were grown to log phase and then treated with the agent of choice (parent, prodrug, or positive control) for 1 hour before irradiation at 0.6 kGy. Surviving fraction compared to that seen in control (untreated) cells, which were not irradiated, was then calculated. The positive control homocysteine thiolactone (HCTL) and WR-1065 showed the greatest amount of protection.

III. Covalent Conjugates of Thiol- or Selenol-Amines and Antioxidant Vitamins

1. Agent Design

The present invention focuses on the antioxidant vitamins C and E, and the thiol or selenol agents, cyst(e)ine, cyst(e)amine, N-acetylcysteine, glutathione, WR-1065/WR-33278, selenocysteine, and selenocysteamine. This represents a minimum of 24 combinations of the two classes. It will be appreciated by those skilled in the art that other antioxidants can be conjugated to these thiol- or selenol-containing compounds.

2. Chemical Synthesis

The schemes below summarize potential approaches using cysteamine for illustrative purposes. Many permutations are available.

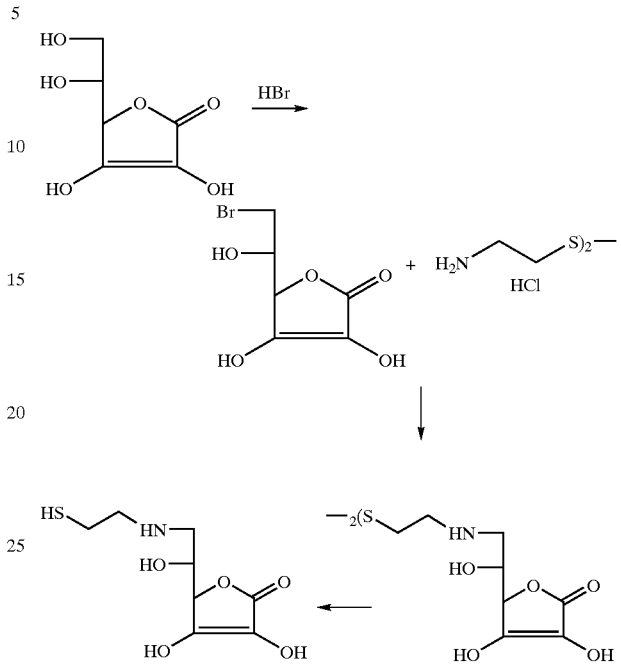

IV. Modified Prodrugs of L-Cysteine of L-Selenocysteine

1. Agent Design

These prodrugs possess a modified carboxyl group compared to unmodified prodrugs of L-cysteine and L-selenocysteine. The purpose of the modification is to reduce the hydrophilicity of the prodrugs and improve their cellular uptake and retention in the body. The modifications include converting the carboxyl group to an ester or amide functionality.

2. Chemical Synthesis

Ester prodrugs were prepared beginning with commercially available L-cysteine methyl or ethyl ester. The ester is combined with an equimolar amount of carbonyl donor, i.e., acetaldehyde, the aldose monosaccharide, D-ribose, or phenyl chloroformate. The amide prodrugs were prepared by the initial synthesis of L-cysteine amides (not commercially available) from L-cysteine and the appropriate amine, such as ammonia, methylamine, or dimethylamine. The synthesized L-cysteine amides were then reacted with an equimolar amount of carbonyl donor, i.e., acetaldehyde, the aldose monosaccharide, D-ribose, or phenyl chloroformate.

Modified prodrugs of L-selenocysteine can be constructed in an identical fashion. However, L-selenocysteine methyl or ethyl ester are prepared by the esterification of L-selenocysteine with methanol or ethanol because these compounds are not commercially available.

For example, the reaction of L-cysteine ethyl ester and D-ribose may be as follows;

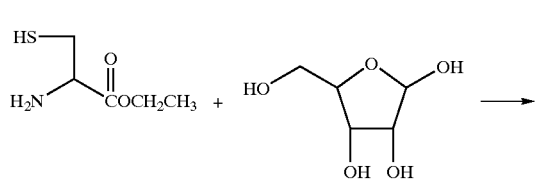

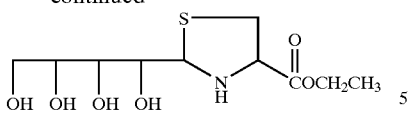

V. Selenazolidines: Modified Prodrugs of Selenocysteine and Selenocysteamine

1. Agent Design

Current selenium supplements rely on inorganic forms. While these forms have some value, they are considered more toxic than necessary, and are unlikely to be useful in cancer chemoprevention or in AIDS supplementation. Several organoselenium compounds, which appear to be less toxic in general than the inorganic forms, have been proposed for in vivo use, but the full potential of this strategy has not yet been realized. In general, however, it is very clear that the chemical form in which selenium is introduced consistently shows a marked influence on biological outcomes. Selenocysteine is an organic form that is present in the body and is now recognized as the 21st amino acid used in protein synthesis. Due to its differential metabolism, it represents the biochemically superior form in which to supply the body with selenium. Unfortunately, selenocysteine is chemically unstable and difficult to handle. Therefore, prodrug forms of the amino acid have been designed which represent chemically superior forms. Similar arguments hold for selenocysteamine as well.

2. Chemical Synthesis

Selenocysteine/selenocysteamine prodrugs can be synthesized by the chemical condensation of the selenolamine with a carbonyl donor. Alkyl or alkyl aldehydes or ketones can be used, including simply donors such as acetaldehyde or benzaldehyde, or aldose or ketose mono- or di-saccharides. In addition, carbonyl donors such as phenyl chloroformate can be used to produce 2-oxo derivatives.

For example, the reaction of L-selenocysteine and phenyl chloroformate is illustrated.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

What is claimed is:

1. A prodrug of the formula:

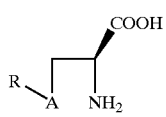

where A is selenium, and R is a mono- di- or oligo-saccharide.

2. A prodrug of claim 1 wherein R is ribose, galactose, glucose, or mannose.

3. A prodrug of the formula:

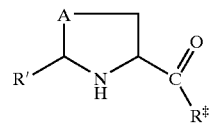

where A is selenium, and
R' is a sugar having the formula $(CHOH)_nCH_2OH$, where n is 1 to 5, or
R' is an alkyl or aryl group, or
R' is =O, and
$R^{\ddagger}$ is an alkoxy, or an amine group.

4. A prodrug of claim 3 wherein $R^{\ddagger}$ is $-OR^1$ where $R^1$ is ethyl, or methyl.

5. A prodrug of claim 3 wherein R' is methyl, ethyl, benzyl, carboxyl, or phenyl.

6. A prodrug as in claim 3 wherein $R^{\ddagger}$ is $-NR^{\dagger}_2$, wherein the $R^{\dagger}$ groups are the same or different and are hydrogen or alkyl.

7. A prodrug as in claim 5 wherein at least one $R^{\dagger}$ is methyl.

8. A method for reducing unwanted side effects of radiotherapy of cancer, in a mammal comprising administering to the mammal the prodrug of claim 1.

9. A method for reducing unwanted side effects of radiotherapy of cancer, in a mammal comprising administering the mammal a prodrug having the formula

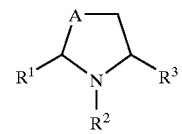

wherein
(1) A is selenium,
$R^1$ is a sugar having the formula $(CHOH)_nCH_2OH$, where n is 1 to 5, or $R^1$ is an alkyl or aryl group, or $R^1$ is =O,
$R^2$ is $CH_2CH_2CH_2N(R^4)_2$, wherein $R^4$ may be the same or different and may be hydrogen, alkyl, alkoxy, or carboxy; and
$R^3$ is hydrogen;
(2) A is selenium,
$R^1$ is a sugar having the formula $(CHOH)_nCH_2OH$, where n is 1 to 5, or $R^1$ is an alkyl or aryl group, or $R^1$ is =O,
$R^2$ is hydrogen, $R^3$ is $COR^5$, wherein $R^5$ an alkoxy, or an amine group; or
(3) A is selenium,
$R^1$ is a sugar having the formula $(CHOH)_nCH_2OH$, where n is 1 to 5, or $R^1$ is an alkyl or aryl group, or $R^1$ is =O, $R^2$ is hydrogen, and $R^3$ is hydrogen or COOH.

10. A prodrug of the formula

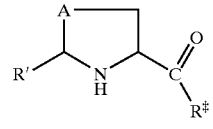

where A is sulfur or selenium, and
$R^1$ is an alkyl or aryl group, or
$R^1$ is =O, and
$R^{\ddagger}$ is an alkoxy, or an amine group.

* * * * *

UNITED STATES PATENT AND TRADEMARK OFFICE
CERTIFICATE OF CORRECTION

PATENT NO. : 6,841,536 B2
DATED : January 11, 2005
INVENTOR(S) : Roberts et al.

It is certified that error appears in the above-identified patent and that said Letters Patent is hereby corrected as shown below:

Column 12,
Line 48, after "$R^5$" and before "an" insert -- is --.

Signed and Sealed this

Twenty-sixth Day of April, 2005

JON W. DUDAS
*Director of the United States Patent and Trademark Office*